United States Patent [19]

Lovell

[11] 4,454,127

[45] Jun. 12, 1984

[54] INSECTICIDAL PYRETHROID COMPOSITIONS

[75] Inventor: James B. Lovell, Pennington, N.J.

[73] Assignee: American Cyanamid Co., Stamford, Conn.

[21] Appl. No.: 443,404

[22] Filed: Nov. 22, 1982

Related U.S. Application Data

[60] Continuation-in-part of Ser. No. 103,897, Dec. 17, 1979, abandoned, which is a continuation of Ser. No. 874,305, Feb. 2, 1978, abandoned, which is a division of Ser. No. 623,864, Oct. 20, 1975, Pat. No. 4,087,523.

[51] Int. Cl.$^3$ ...................... A01N 37/34; A01N 57/00
[52] U.S. Cl. ...................................... 424/218; 424/304
[58] Field of Search ................................ 424/218, 304

[56] References Cited

U.S. PATENT DOCUMENTS 3,502,720  3/1970  Arndt ................................. 260/564
3,966,959  6/1976  Addor ................................ 424/304

OTHER PUBLICATIONS

Chem. Week; Jun. 21, 1972.
Pesticide Index 4th Ed., 1969, Frear, pp. 285 & 372.

*Primary Examiner*—Allen J. Robinson
*Attorney, Agent, or Firm*—H. G. Jackson

[57] ABSTRACT

This invention relates to novel insecticidal compositions comprising a m-phenoxybenzyl ester of a spirocarboxylic acid and an insecticidal agent of O,O-dimethyl-O-p-nitrophenyl phosphorothioate; and to the use of the above compositions for protecting agricultural crops from attack by insect pests.

6 Claims, No Drawings

INSECTICIDAL PYRETHROID COMPOSITIONS

This application is a continuation-in-part of co-pending Ser. No. 103,897 filed Dec. 17, 1979 now abandoned which is a continuation of abandoned Ser. No. 874,305 filed Feb. 2, 1978 now abandoned which is a division of Ser. No. 623,864 filed Oct. 20, 1975 which is now U.S. Pat. No. 4,087,523.

The field of the invention is pyrethroids in combination with selected insecticidal agents for the control of insect pests, particularly those which are of major economic importance to the cotton industry.

Pyrethrin-like compounds (pyrethroids) are known in the chemical art. Many such compounds have been shown to possess insecticidal properties, but most have failed to provide entirely satisfactory insect and/or acarina control. None, to the best of our knowledge, has been entirely satisfactory for the control of the complex of insects which ravage growing cotton plants; and with few exceptions, all have been subject to extremely rapid degradation to non-toxic substances. This latter property has been recognized as a major deficiency of the pyrethroids. While such compounds have provided excellent knockdown of many insects, rapid degradation of said compounds has resulted in lack of residual insect control even for a few days.

The pyrethroids useful in my invention are described in R. W. Addor's U.S. Pat. No. 3,966,959 (1976).

Heretofore, many conventional insecticidal chemicals have also been employed for the control of insects which ravage growing cotton plants. Many have met with a high degree of acceptance by cotton growers, but virtually all have been found to have their limitations and none has afforded complete protection for the growing cotton plants against the insect complex encountered.

It is therefore an object of the present invention to provide an insecticidal composition which is highly effective for protecting crops, particularly cotton crops, from insect attack.

It is also an object of this invention to provide a chemical composition which is more effective for controlling certain Lepidopterous, Hemipterous and Coleopterous insects and more effective for protecting important agronomic crops from attack by the insects, than the single ingredients.

Advantageously, the compositions of the invention are useful as contact or stomach poisons. They are superior in insecticidal activity or insect repellancy, to the pyrethroid alone or the phosphate insecticide and can be employed as protecting agents for important agronomic crops such as cotton, soybeans, tobacco, cole crops, leafy vegetables, forage crops, corn, snapbeans, and tomatoes.

This invention relates to insecticidal compositions comprising (a) a phenoxybenzyl ester of a spirocarboxylic acid having a formula of:

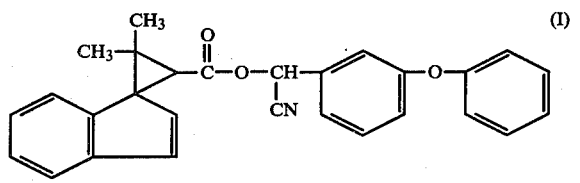

More particularly, this invention relates to novel insecticidal compositions in which the ratio of the conventional insecticide to the pyrethroid is from 5:4 to 40:1 and preferably 5:4 to 20:1. Still more particularly, the compositions of this invention are applied to foliage of plants, which are to be protected from insect attack, in amounts sufficient to provide from about 1.0 to 5.0 oz and preferably 1.6 to 3.2 oz of the pyrethroid and from 0.25 to 4.0 lbs per acre of the conventional insecticide. These most preferred rates are equivalent to 0.11 to 0.22 kg/hectare of the pyrethroid and from 0.28 to 4.48 kg/hectare of the conventional insecticide.

In accordance with this invention the phenoxybenzyl esters of benzospirocarboxylic acids depicted by formula I, can be prepared by reacting approximately equimolar amounts of an acid halide, preferably the chloride of a benzospirocarboxylic acid (IV) and m-phenoxybenzyl alcohol (V). The reaction is generally conducted in the presence of a suitable solvent such as benzene, toluene, diethyl ether, or the like, at a temperature between about 10° C. and 30° C., and in the presence of an acid acceptor such as an organic tertiaryamine such as triethylamine, trimethylamine, pyridine, or the like. The reaction can be graphically illustrated as follows:

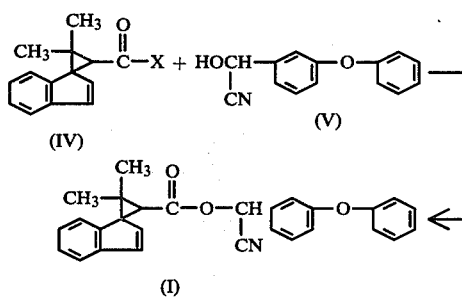

wherein $R_1$ is cyano.

The benzospirocarboxylic acid halide (IV) is readily obtained by reaction of the appropriate benzospirocarboxylic acid (III) with a thionyl halide such as thionyl chloride, thionyl bromide or a phosphorus halide such as phosphorus trichloride or phosphorus pentachloride in the presence of an organic solvent such as toluene, benzene or benzenehexane mixture. This reaction may be conducted at room temperature but is preferably conducted at 60°–90°; and can be illustrated as follows:

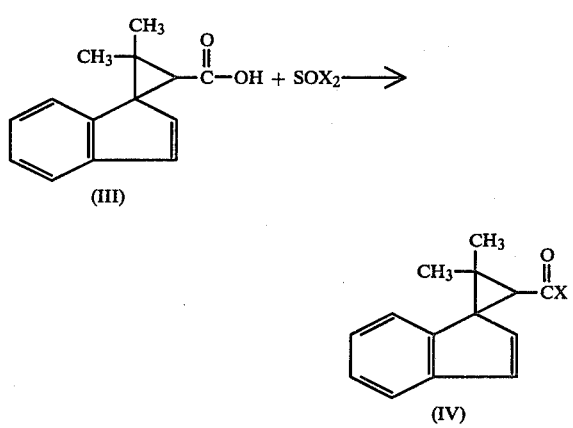

The formula II phenoxybenzyl esters of spirocarboxylic acids can be prepared in a manner similar to that described above for the preparation of the formula I benzospiro compounds, by substituting the appropriate spirocarboxylic acid (VI) for the above-mentioned benzospirocarboxylic acid (III); converting said acid to its corresponding acid halide (VII) and reacting the thus-formed acid halide with m-phenoxybenzyl alcohol (V), under the conditions mentioned above, to obtain the formula (II) m-phenoxybenzyl ester of the spirocarboxylic acid. This reaction can be graphically illustrated as follows:

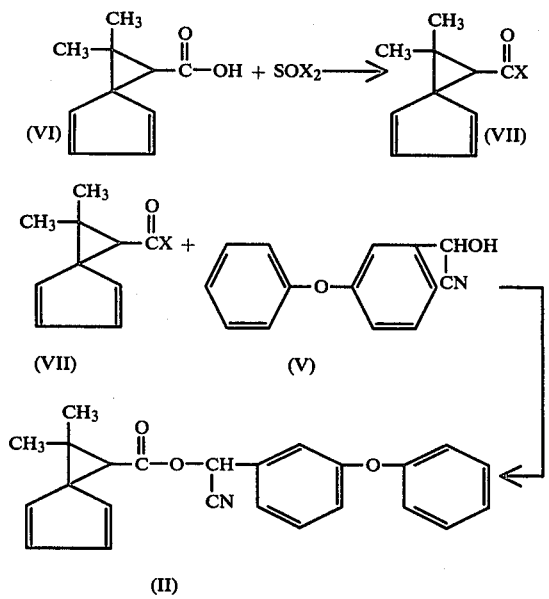

wherein X is halogen, preferably chloro, and R₁ is cyano.

In accordance with this invention, it should also be understood that various geometric isomers as well as optical isomers of the above-identified compounds do result from the preparations described. In the preparation of the α-cyano-m-phenoxybenzyl ester, an additional chiral center is introduced, and this allows for additional d, l pairs.

For the control of insects, including soil insects, which attack growing plants and/or harvested crops, including stored grain, the insecticidal compositions of this invention may be applied to the foliage of plants, the insect's habitat and/or the insect's food supply. Generally, the active composition is applied in the form of a dilute liquid spray; however, it may also be applied as an aerosol, a dust, wettable powder, or the like.

Liquid sprays which are particularly useful are oil sprays and emulsifiable concentrates which can be further diluted for application.

A typical emulsifiable concentrate useful for protecting a variety of crops such as cereals, cole crops, cucurbits, ornamentals, shrubs, and the like, may comprise about 24% by weight of the active composition; 4% by weight of an emulsifying agent, conventionally employed in the preparation of pyrethroid formulations: 4% by weight of a surfactant; 23% by weight of an organic solvent such as cyclohexanone; and about 45% by weight of a petroleum solvent having a minimum aromatic content of about 93 volume %.

Typical compositions of this invention which are highly effective for controlling insect pests and or protecting crops from attack thereby are as follows.

| Typical Preferred Compositions of the Present Invention | | | |
|---|---|---|---|
| Chemical | Rate of Chemical kg/ha | *Pyrethroid Rate kg/ha | Ratio of Chemical To Pyrethroid |
| Methyl Parathion | 0.28–1.68 | 0.11–0.22 | 5–4 to 15–1 |

The invention is further demonstrated by the non-limiting examples provided below.

EXAMPLE 1

Preparation of 2,2-dimethyl-4,5-benzospiro[2,4]hepta-4,6-diene-1-carboxylic acid, α-cyano-m-phenoxybenzyl ester.

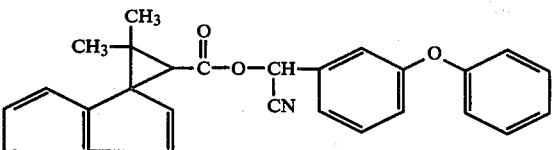

2,2-Dimethyl-4,5-benzospiro[2,4]hepta-4,5-diene-1-carboxylic acid, 3.4 g, is dissolved in 100 ml of a hexane/benzene (4:1) solution. Thionyl chloride, 15.0 g, is then added and the solution is stirred for 12 hours. Refluxing is carried out for 20 minutes, and the volume is reduced in vacuo to remove solvents and excess thionyl chloride. The acid chloride is used directly without further purification. The acid chloride is taken up in 20 ml of benzene and is added dropwise to a solution of 3.1 g of a α-cyano-m-phenoxybenzyl alcohol and 1.0 g of pyridine in 100 ml of benzene. After 4 hours, the precipitate is filtered, and the filtrate reduced in vacuo to give a viscous oil. Purification by column chromatography on silica gel with elution by chloroform/hexane (1:2) gives 1.3 g of pale yellow oil which exhibits the following spectral properties: infrared spectrum (neat film). 1730 cm⁻¹; nuclear magnetic resonance spectrum (CDCl₃): δ=6.8–7.6

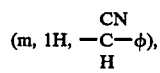

6.22 (d, 0.5H, vinyl), 2.73

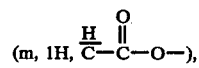

1.72–1.43 (m, 6H, methyls).

EXAMPLE 2

Effectiveness of Chemical Compositions Against Adult Boll Weevils (*Anthonomus grandis*) on Cotyledons of Cotton Plants To determine the effectiveness of test compositions for controlling boll weevils and/or protecting plants from their attack, cotyledons from Stoneville #213 cotton plants are dipped in solutions of test compositions and then permitted to dry. After drying, these treated cotyledons are placed in individual 9.0 cm petri dishes with moist Whatman #1 filter papers on the bottom thereof. Ten adult boll weevils are then placed in each of the dishes and the dishes are covered and placed in a room maintained at 26° C. and 30% relative humidity. After 3 days, mortality counts are made and the amount of feeding is estimated.

Data obtained are reported in the Table I below, where it can be seen that a composition containing 100 ppm of 2,2-dimethyl-4,5-benzospiro[2,4]hepta-4,6-diene-1-carboxylic acid, α-cyano-m-phenoxybenzyl ester and 3 ppm of methyl parathion provides 100% control of adult boll weevils; whereas, 100 ppm of the ester alone provides only 32% control of said boll weevils and 3 ppm of methyl parathion alone provides only 20% control of these insects.

TABLE I

Effectiveness of Compositions for Controlling Adult Boll Weevils on Cotyledons of Cotton Plants

| Compound or Composition | Concentration ppm | % Mortality | % Feeding Damage |
|---|---|---|---|
| 2,2-Dimethyl-4,5-benzospiro[2,4]-hepta-4,6-diene-1-carboxylic acid, α-cyano-m-phenoxybenzyl ester | 100 | 32 | 3 |
| Methyl parathion | 3 | 20 | 25 |
| Methyl parathion plus 2,2-Dimethyl-4,5-benzospiro[2,4]hepta-4,6-diene-1-carboxylic acid, α-cyano m-phenoxybenzyl ester | 3 + 100 | 100 | 5 |

EXAMPLE 3

Evaluation of Chemical Composition for the Control of Bean Aphids (*Aphid fabae Scopoli*)

A two-inch square fiber pot containing a nasturtium plant which is infested with approximately 100 aphids 2 days prior to test initiation, is placed on a 4 rpm turntable located in an exhaust hood. The plant and aphids are sprayed directly with the test solution for 2 revolutions of the turntable with a DeVilbiss atomizer at 20 psi air pressure. The spray tip is held 6 to 8 inches from the plant during spraying and after spraying the pot with plant and aphids is laid on its side on a white enamel tray. One day after treatment the plants are examined and mortality counts are made. Data obtained are reported in Table II below, where it can be seen that compositions containing 1 ppm of methyl parathion and either 0.3 ppm of 2,2-dimethyl-4,5-benzospiro[2,4]-hepta-4,6-diene-1-carboxylic acid, α-cyano-m-phenoxybenzyl ester, provide 99 to 100% control of bean aphids; whereas, 1 ppm of methyl parathion alone provides only 50% control of bean aphids, 0.3 ppm of the m-phenoxybenzyl ester alone provides only 7% control of bean aphids and 0.03 ppm of the α-cyano-m-phenoxybenzyl ester alone provides only 12% control of said insect pests.

TABLE II

Effectiveness of Chemical Compositions for Controlling Bean Apids (*Aphid fabae* Scopoli)

| Chemical or Composition | Concentration ppm | % Mortality |
|---|---|---|
| Methyl Parathion | 1 | 50 |
| 2,2-Dimethyl-4,5-benzospiro[2,4]hepta-4,6-diene-1-carboxylic acid,α-cyano-m-phenoxybenzyl ester | 0.03 | 12 |
| Methyl parathion plus the | 1.0 | |
| α-cyano-m-phenoxybenzyl ester (identified above) | + 0.03 | 100 |

What is claimed is:

1. An insecticidal composition comprising (i) a phenoxybenzyl ester of a spirocarboxylic acid having a formula:

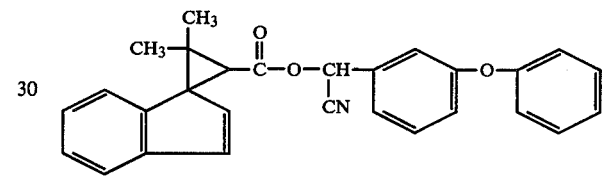

and (ii) O,O-dimethyl-O-p-nitrophenyl phosphorothioate and a diluent wherein the concentration of ester is from about 0.03 to 100 ppm and the concentration of phosphorothioate is from about 1 to 3 ppm.

2. A composition according to claim 1 containing about 100 ppm of the phenoxybenzyl ester of the spirocarboxylic acid and about 3 ppm of the O,O-dimethyl-O-p-nitrophenyl phosphorothioate.

3. A composition according to claim 1 containing about 0.03 ppm of the phenoxybenzyl ester of the spirocarboxylic acid and about 1.0 ppm of the O,O-dimethyl-O-p-nitrophenyl phosphorothioate.

4. A method for the control of insect pests comprising applying to the insects habitat, their food supply or their breeding sites, an insecticidally effective amount of a composition comprising (i) a phenoxyphenyl ester of a spirocarboxylic acid in a concentration from about 0.03 to 100 ppm having a formula:

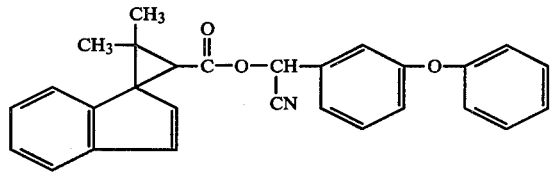

and (ii) O,O-dimethyl-O-p-nitrophenyl phosphorothioate in a concentration from about 1 to 3 ppm and a diluent.

5. A method according to claim 4 for the control of Lepidopterous, Hemipterous and Coleopterous.

6. A method for the control of insect pests according to claim 4 in cotton crops.

* * * * *